United States Patent
Eddy et al.

(10) Patent No.: US 8,986,581 B2
(45) Date of Patent: Mar. 24, 2015

(54) BIOCHAR PRODUCTS AND METHOD OF MANUFACTURE THEREOF

(71) Applicant: Carbon Basis Company Ltd., Edmonton (CA)

(72) Inventors: Leonard Bruce Eddy, Beaumont (CA); Jack Wolstenholme, Sarnia (CA); Paul Byron Tiege, Red Deer County (CA); Nancy Yadira Meza Trevino, Torreon Coahuila (MX); Jesus Josafath Quezada Rivera, Torreon Coahuila (MX)

(73) Assignee: Carbron Basis Company Ltd., Edmonton, Alberta (CA)

( * ) Notice: Subject to any disclaimer, the term of this patent is extended or adjusted under 35 U.S.C. 154(b) by 0 days.

(21) Appl. No.: 13/951,050

(22) Filed: Jul. 25, 2013

(65) Prior Publication Data

US 2014/0030250 A1 Jan. 30, 2014

Related U.S. Application Data

(60) Provisional application No. 61/676,399, filed on Jul. 27, 2012.

(51) Int. Cl.
  *B29C 47/00* (2006.01)
  *C05F 11/02* (2006.01)
  (Continued)

(52) U.S. Cl.
  CPC .............. *C05G 3/0058* (2013.01); *A61K 33/44* (2013.01); *B01J 20/24* (2013.01); *B01J 31/06* (2013.01);
  (Continued)

(58) Field of Classification Search
  USPC .................................. 71/11–63; 264/15, 118
  See application file for complete search history.

(56) References Cited

U.S. PATENT DOCUMENTS

| | | |
|---|---|---|
| 2,684,295 A | 7/1954 | Eyster |
| 3,295,950 A | 1/1967 | Blouin et al. |

(Continued)

FOREIGN PATENT DOCUMENTS

| | | |
|---|---|---|
| CN | 1704382 A | 12/2005 |
| GB | 1171255 A | 11/1969 |

(Continued)

OTHER PUBLICATIONS

"[Biochar] Biochar with clay", tech.groups.yahoo.com/group/biochar/message/306, Yahoo Mail.

(Continued)

*Primary Examiner* — Wayne Langel
(74) *Attorney, Agent, or Firm* — Brion Raffoul

(57) ABSTRACT

A method for producing biochar particles or pellets which use sulphur and other additives. The method includes producing a mixture with biochar and additives selected from sulphur, lignin, and gluten. The mixture is mixed with water and passed through an extruder to produce an extrudate. The extrudate is then cut into pellets. The pellets are then tumbled/spun with each other and heated to result in mostly spheroidal pellets whose mechanical characteristics allow them to be used with well-known agricultural equipment. The biochar can be produced with sulphur incorporated as an outer coating. To produce this sulphur coated biochar, the method includes feeding a biomass feedstock to a pyrolysis reactor, pyrolyzing the feedstock into biochar particles, size-sorting the biochar particles, and coating the biochar particles with the sulphur coating material.

11 Claims, 2 Drawing Sheets

(51) Int. Cl.

| | |
|---|---|
| *C05G 3/00* | (2006.01) |
| *A61K 33/44* | (2006.01) |
| *B01J 20/24* | (2006.01) |
| *B01J 31/06* | (2006.01) |
| *B01J 27/02* | (2006.01) |
| *B01J 20/20* | (2006.01) |
| *B01J 20/30* | (2006.01) |
| *B01J 20/32* | (2006.01) |
| *B01J 20/28* | (2006.01) |

(52) U.S. Cl.
CPC *B01J 27/02* (2013.01); *B01J 20/20* (2013.01); *C05G 3/00* (2013.01); *B01J 20/3007* (2013.01); *B01J 20/3028* (2013.01); *B01J 20/3042* (2013.01); *B01J 20/3078* (2013.01); *B01J 20/3204* (2013.01); *B01J 20/3234* (2013.01); *B01J 20/28019* (2013.01); *C05F 11/02* (2013.01); *B01J 2220/4837* (2013.01); *B01J 2220/485* (2013.01); *Y02E 50/13* (2013.01)
USPC .................................. 264/15; 71/24; 264/118

(56) References Cited

U.S. PATENT DOCUMENTS

| | | | |
|---|---|---|---|
| 3,342,577 | A | 9/1967 | Blouin et al. |
| 3,576,613 | A | 4/1971 | Fleming |
| 3,837,835 | A | 9/1974 | Weinrotter et al. |
| 3,903,333 | A | 9/1975 | Shirley, Jr. et al. |
| 4,460,612 | A | 7/1984 | Saleeb et al. |
| 4,587,358 | A | 5/1986 | Blouin |
| 4,857,243 | A * | 8/1989 | Von Blucher et al. .......... 264/13 |
| 5,407,442 | A | 4/1995 | Karapasha |
| 5,454,851 | A | 10/1995 | Zlotnikov et al. |
| 5,466,274 | A | 11/1995 | Hudson et al. |
| 5,676,727 | A | 10/1997 | Radlein et al. |
| 5,788,896 | A | 8/1998 | Bertram et al. |
| 5,944,960 | A | 8/1999 | Nakata et al. |
| 6,287,496 | B1 * | 9/2001 | Lownds .......... 264/118 |
| 6,818,579 | B2 | 11/2004 | Giangrasso |
| 7,947,155 | B1 | 5/2011 | Green et al. |
| 8,012,533 | B2 | 9/2011 | Smith et al. |
| 8,361,186 | B1 * | 1/2013 | Shearer et al. ...... 71/32 |
| 8,709,122 | B2 * | 4/2014 | Lee et al. .......... 71/54 |
| 2004/0111968 | A1 | 6/2004 | Day et al. |
| 2007/0169527 | A1 | 7/2007 | Wynnyk et al. |
| 2008/0040975 | A1 | 2/2008 | Calderon |
| 2009/0126433 | A1 | 5/2009 | Piskorz et al. |
| 2010/0162780 | A1 * | 7/2010 | Scharf ............. 71/36 |
| 2010/0312008 | A1 | 12/2010 | Kastner et al. |
| 2012/0125064 | A1 * | 5/2012 | Joseph et al. ...... 71/27 |

FOREIGN PATENT DOCUMENTS

| | | |
|---|---|---|
| GB | 1397355 A | 6/1975 |
| JP | 61138512 A | 6/1986 |
| JP | 08245280 A | 9/1996 |
| JP | 2004336042 A | 12/2004 |
| KR | 20030013491 A | 2/2003 |
| WO | 8911462 A1 | 11/1989 |
| WO | 9429239 A1 | 12/1994 |
| WO | 2010129988 A1 | 11/2010 |

OTHER PUBLICATIONS

Amir Mendi Dehkhoda, "Developing Biochar-Based Catalyst for Biodiesel Production", University of British Columbia, Aug. 2010.
"Effects of mycorrhizal fungi and biochar 75 days", www.energeticforum.com/agriculture/1647-effects-mycorrhizal-fungi-biochar-5-days.html, energetic forum.
Lawrence H Keith, "Final Report: Commercialization of Solid Acid and Base Catalysts Derived from Biochar Optimized to Produce Biodiesel from Low Cost Oils", cfpub.epa.gov/ncer_abstracts/index.cfm/fuseaction/display.abstractDetail/abstract/9125/report/F, USEPA.
Manuel Garcia-Perez et al, "Methods for Producing Biochar and Advanced Bio-fuels in Washington State, Part 3: Literature Review, Technologies for Product Collection and Refining", Department of Ecology State of Washington, Washington State University.
"Agrichar Biochar as a Soil Amendment", (2010) Pacific Pyrolysis, The Australian and New Zealand Biochar Researchers Network, Pacific Pyrolysis Pty Ltd.
SumiBall Ltd, "Sumi Ball", www.sumiball.com.
"Tiger 90CR Sulphur", www.tigersul.com/products/agriculture/bentonite-sulphor/tiger-90-cr-sulphur.html, Tiger-Sul.
Joyleene T Yu et al, "Development of Biochar-based Catalyst for Transesterification of Canola Oil", Energy Fuels 2011, 25, pp. 337-344.
A M Dehkhoda et al, "Biochar Based Solid Acid Catalyst for Biodiesal Production", Applied Catalysis, 2010, vol. 382, pp. 197-204.
G M Hill et al, "Effect of Sulphur Levels in Urea-Treated Corn Silage Diets [Cattle Diets]", Sulphur-in-agriculture (USA). 1984. v. 8 p. 8-10.
JR Kastner et al, "Catalytic Esterification of Fatty Acids Using Solid Acid Catalysts Generated from Biochar and Activated Carbon", Catalysis Today, 2012, vol. 190, issue 1, pp. 122-132.
Hasan Rustu Kutlu et al, "Effects of Providing Dietary Wood (Oak) Charcoal to Broiler Chicks and Laying Hens", Animal Feed Science and Technology, vol. 90, issues 3-4, Apr. 16, 2001, pp. 213-226.
M Morrison et al, "Nutrient Metabolism and Rumen Micro-Organisms in Sheep Fed a Poor-Quality Tropical Grass Hay Supplemented With Sulphate", The Journal of Agriculture Science, vol. 115, issue 2, Oct. 1990, pp. 269-275.
Samuel L Tisdale, "Sulphur in Forage Quality and Ruminant Nutrition", Washington: Sulphur Institute, 1977, v 13.
H-C Mundt et al., "Control of Coccidiosis due to *Eimeria bovis* and *Eimeria zuernii* in Calves with Toltrazuril under Field Conditions in Comparison with Diclazuril and Untreated Controls", Parasitol Resistance (2007), 101 (Supplement 1): 93-104, 17661113, Cit:2.
Katsumi Naka et al., "Adsorption Effect of Activated Charcoal on Enterohemorrhagic *Escherichia coli*", Nov. 2000.
S. Watarai et al., "Feeding Activated Charcoal from Bark Containing Wood Vinegar Liquid (Nekka-Rich) Is Effective as Treatment for Cryptosporidiosis in Calves", American Dairy Science Association, 2008, Journal of Dairy Science vol. 91 No. 4, 2008, pp. 1458-1463.
R. Kasten Dumroese et al., "Pelleted biochar: Chemical and physical properties show potential use as a substrate in container nurseries", www.elsevier.com/locate/niombioe, Biomass and Bioenergy 35 (2011) 2018-2027.

* cited by examiner

BIOCHAR PRODUCTS AND METHOD OF MANUFACTURE THEREOF

TECHNICAL FIELD

The present invention relates to a biochar or charcoal product and methods of producing the biochar product which incorporates different additives.

BACKGROUND OF THE INVENTION

Biochar is a highly porous carbonized material that can be found on the soil after a forest has burned. The porous nature of biochar and other charcoal products has been found to provide a habitat for beneficial microbes that absorb toxins in the soil and convert organic detritus into useful materials for the growth of nascent plants.

Synthetic charcoal products and biochar can be made on an industrial scale by burning wood chips and other cellulosic materials in an oxygen deficient atmosphere. Biochar in particular has a remedial benefit on the soil due mainly to the highly porous nature of the charcoal it contains. These pores are able to absorb toxic metals and accommodate beneficial microbes that feed on the remaining organics, leaving the soil fit for plant growth.

Synthetic biochar is made and traded worldwide. It is used mainly for soil remediation and improved plant growth. Early manufacturing processes were essentially based upon those for making pure charcoal. The feedstock can be any cellulose containing material that will breakdown under anoxic conditions to produce charcoal. Wood chips are preferred. Although the cellulose in the wood decomposes mainly to carbon and water, at high temperatures, a side reaction converts some charcoal into biogases and bioliquids. As biochar is not a pure charcoal, it is sold at a lower price. The reaction by-products reduce the value further, as they are only marketable as cheap fuel.

The particles of synthetic biochar may be distributed on the soil with equipment used for other agricultural products, such as plant seed and pelletized fertilizer. However, since the charcoal in the biochar is somewhat friable, distribution using conventional agriculture equipment creates hazardous dust, and loss of useful product. Furthermore, the low bulk density and lack of particle sizing control of the biochar causes separation of any blend of biochar and plant seed and/or commercial fertilizer during handling and distribution. To overcome this problem, methods have been developed to protect the biochar particles with a layer of an inert ceramic material. This approach has been found to minimize product breakdown and increase bulk density. As the ceramic coating needs to be sintered at high temperature, undesirable by-products are formed at the expense of some of the charcoal. Also, the inert coating simply disintegrates into small particles that remain in the soil.

Ceramic coatings are typically applied as slurry to the cellulosic biomass feedstock as they are fed into the reactors. The reactors then convert the feedstock into biochar and sinter the ceramic coating in a single step. U.S. Pat. No. 5,944,960 teaches a system that includes a flame inside the reactor that is fed by biogas produced as a process by-product, to generate heat for the pyrolysis and ensure the absence of oxygen in the reaction zone.

Sintering the ceramic coating requires reactor temperatures of around 800° C. to 900° C., although the interior temperatures of the particles may be lower, due to the coating's inhibition of heat conduction and the porosity of the particles.

It has been established that a pyrolysis temperature of around 450° C. produces the highest porosity charcoal content in the biochar. At this temperature, by-product reactions are suppressed, leading to the maximum production of charcoal in the pellets. Therefore, a coating that can be sintered at a lower temperature range while not increasing production costs or complexity is desirable in the industry.

It should be noted that biochar may also be used in other industries. Biodiesel for sale as transportation fuel in Canada and the United States must meet strict quality guidelines (CAN/CGSB-3.524-2011 in Canada and ASTM 6751 in the U.S.). Biodiesel must have low water and glycerol content. Often biodiesel manufacturers must use post-manufacturing desiccants and absorptive resins to remove unwanted contaminants before the quality of the biodiesel is sufficient for sale. This is sometimes referred to as "polishing." A biochar-based polishing agent would be advantageous because it is environmentally benign unlike some polymeric polishing agents. Thus, disposal of the bio-based based agent after polishing may be seen as having less of a negative impact. Because biochar is dusty and comprised of small particles that would contaminate the biodiesel, using un-pelleted biochar is not an option to absorb unwanted liquid contaminants such as water from transportation fuel. However, if biochar is densified into pellets that are robust and non-dusty, the product can be used as a polishing agent without introducing further contamination.

Biodiesel manufacturing is still most commonly performed using metal methoxide chemistry (e.g. sodium or potassium methoxide catalyzed transesterification). This manufacturing process requires that the feedstock material have very low free fatty acid content. Free fatty acids present in the feedstock react quantitatively with basic metal methoxides to form soap. Soap formation decreases yield and is an unwanted contaminant. Soap also causes and supports an emulsion between the organic and aqueous phases, which complicates phase separation and can diminish yield. The requirement for low free fatty acids in feedstock means that high quality or highly processed vegetable oils are used, which can be quite expensive in comparison to the selling price of the finished biodiesel product. Biodiesel manufacturing could be more profitable if lower quality feedstocks with high free fatty acid content, such as waste cooking oil, could be easily used. Two scenarios are possible considering conversion of high free fatty acid oils to biodiesel:

1) free fatty acids are removed or converted to alkyl esters (i.e. biodiesel). This allows the resulting oil mixture to be used in metal methoxide biodiesel production. This type of catalysis is most commonly associated with solid acid catalysts 2) direct conversion of the high FFA feedstock to biodiesel. This requires that the catalyst used catalyzes both esterification and transesterification reactions. This conversion can be done using heterogeneous liquid or gaseous acids such as sulfuric acid or hydrochloric acid. Neither is ideal because the finished product can carry acid and therefore a unit operation is required to remove acid from the biodiesel. A solid-acid catalyst obviates this concern because the acid moieties are bound to the solid catalyst and are not carried through to the final product.

Sulfonated biochar can catalyze esterification of free fatty acids to biodiesel in mixtures containing vegetable oil.

There are products on the market that can be used as solid acid catalysts for esterification of free fatty acids in oil. This procedure is generally known as "pre-esterification" because the esterification of the free fatty acids to biodiesel happens prior to the transformed mixture entering the usual metal methoxide biodiesel manufacturing process. Most solid acid catalysts for this pre-esterification procedure are sulfonated macroreticular cross-linked polyvinylchloride resins. That is, the catalyst is generally in the form of a small bead, which is made of cross-linked polyvinylstyrene. The morphology of the beads is quite rough, allowing the beads to have high surface area and therefore greater surface for catalysis. The active catalytic sites are pendant sulfonic (—$SO_3H$) groups. A biochar catalyst is bio-based when considering disposing spent catalyst in a landfill.

A biochar catalyst that can be used in the above process would therefore be advantageous. Not only that, but a process for producing such a catalyst, with mechanical properties that allow its use in the biodiesel industry, would also be advantageous and desirable.

SUMMARY OF INVENTION

The present invention provides a method for producing biochar particles or pellets which use sulphur and other additives. The method includes producing a mixture with biochar and additives selected from sulphur, lignin, and gluten. The mixture is mixed with water and passed through an extruder to produce an extrudate. The extrudate is then cut into pellets. The pellets are then tumbled/spun with each other and heated to result in mostly spheroidal pellets whose mechanical characteristics allow them to be used with well-known agricultural equipment. The biochar can be produced with sulphur incorporated throughout the mixture as a binding agent or as an outer coating. To produce this sulphur coated biochar, the method includes feeding a biomass feedstock to a pyrolysis reactor, pyrolyzing the feedstock into biochar particles, size-sorting the biochar particles, and either mixing sulfur with the biochar powder prior to further processing or coating the biochar particles with the sulphur coating material.

In a first aspect, the present invention provides a method for producing biochar pellets, the method comprising:
 a) mixing biochar with at least one additive and water to result in a mixture;
 b) extruding said mixture to result in an extrudate;
 c) cutting said extrudate into pellets;
 d) heating said pellets for a predetermined time at a predetermined temperature and then cooling said pellets; and
 e) processing said pellets in a spheronization device which heats said pellets and forces said pellets to tumble against one another while being heated.

In a second aspect, the present invention provides a method for producing biochar particles coated with a coating material comprising sulphur, said method comprising the steps of:
 a) feeding a biomass feedstock to a pyrolysis reactor, to pyrolize the feedstock into biochar particles;
 b) size-sorting the biochar particles;
 c) mixing said biochar particles with at least one additive and water to result in a mixture;
 d) extruding said mixture to result in an extrudate;
 e) cutting said extrudate into pellets;
 f) heating said pellets for a predetermined time at a predetermined temperature and then cooling said pellets;
 g) processing said pellets in a spheronization device which heats said pellets and forces said pellets to tumble against one another while being heated;
wherein said at least one additive is selected from a group comprising gluten, sulphur, and lignin.

In a third aspect, the present invention provides a biochar product comprising a porous biochar pellet having additives selected from a group comprising gluten, sulphur, and lignin.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
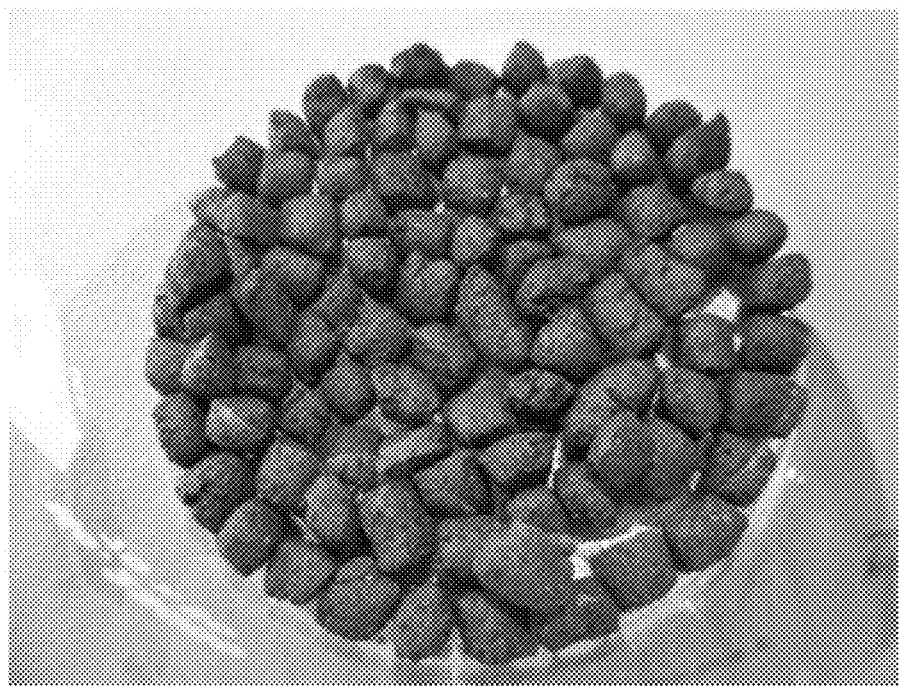
FIGS. 1-4 are illustrations of the various biochar pellets produced according to the varying procedures detailed below.

The present invention, in one embodiment, provides a coated biochar or charcoal product having a coating and binding agent which may include sulphur and/or gluten. The coating would both protect and increase overall bulk density. The present invention also provides a method of manufacturing such a coated biochar product.

By increasing bulk density and adding a protective coating, as well as promoting the spheronization of the pellets, the handling characteristics of the final product are improved. This, in turn, allows easier product distribution by conventional agriculture fertilizer spreading equipment. The bulk density and diameter of the present coated biochar particles may be modified to match that of commercial fertilizer particles by adjusting the mixture formulation, the coating procedure, as well as the formation of the pellet size.

Some important properties of biochar include the ability to absorb nutrients, metals and water, as well as provide physical space to host soil micro-flora and micro-fauna. These properties are found to be highly variable depending on a number of conditions including: biomass feedstock type, shape and moisture content, pyrolysis heating rate, highest heating temperature, reaction pressure, vessel conditions, and pre-treatment.

It is well understood that the chemical composition of the biomass has a direct impact on the physical nature of the biochar produced and that thermal decomposition of the organic material changes with temperature. As the temperature rises the cellular water evaporates, the organics undergo thermo-chemical decomposition and finally the mineral content appears as ash that, in turn, can sinter under even higher temperatures.

Elemental sulphur primarily exists in the form of an eight-membered ring that melts at about 120-124° C. and boils at about 445° C., which is approximately similar to the temperature range for pyrolyzing cellulosic biomass feedstock into biochar. Upon heating liquid sulfur to ~159 degrees C., inter- and intra-molecular radical chain formation results in an equilibrium mixture of sulfur rings of 8-35 sulfur atoms. Left at this temperature for enough time, elemental sulfur will polymerize into polymeric sulfur of high molecular weight. During this radical polymerization, sulfur radical may form new bonds with other materials that are present as well as form interpenetrating networks, causing physical entanglement. Sulphur is also readily available at a low price, because it is a by-product of oil refining operations.

In one embodiment of the invention, the biochar product is coated with sulphur and, optionally, other additives. The coating of the present invention comprises sulphur as well as other components, additives and impurities including, but not limited to inert substances such as chalk or clay. The sulphur content of the present coating is preferably in the range of from 50 to 100% by weight and more preferably 95 to 100% by weight.

For the purposes of the present invention, the terms biochar and charcoal are used interchangeably and it would be understood to a person of skill in the art that, although biochar and charcoal differ somewhat with respect to feedstock and preparation, the present invention can be applied to a coated biochar or charcoal.

The sulphur-containing coating of the present invention can be applied during the pyrolysis process, at typical biochar pyrolysis temperatures of from 400° C. to about 500° C., to thereby maximize porosity of the biochar. At these temperatures, sulphur contained in the coating material is in the gaseous phase, and will cool to form a coating as the biochar particles are cooled.

As an alternative to the above, the sulphur can be added to biochar at room temperature, then processed at a temperature sufficient to cause melting and radical polymerization of the sulphur so that when the sulphur cools it binds the biochar together as a solid pellet.

By-products of the present process are biogases and bioliquids. These biogases and bioliquids can optionally be fed back to the pyrolysis reactor and burned to supply at least a portion of the heat required for the pyrolysis process.

Alternatively, the sulphur-containing coating material can be added to the pyrolysis reactor after pyrolysis is complete. In such cases, latent heat from the pyrolysis reaction serves to melt the coating material and coat the biochar particles.

The sulphur-containing coating can be added to the reaction as either a liquid or a solid. It is preferable that the coating be added in liquid or solid powder form as liquid or powdered material allows for better control of the thickness and evenness of the coating. The sulphur-containing coating can be applied during the pyrolysis process, as described above, or can be applied outside of the pyrolysis zone. Preferably, the coating material is added to the particles in a zone of lower temperature.

In one example, the sulphur-containing coating material can be added into a cooling zone, commonly in the form of a cooling drum or rack, located after the pyrolysis reactor. The cooling zone is used to allow the biochar pellets to cool prior to storage and shipment. The pellet temperatures in passage from the reactor to cooling zone, and in the cooling zone range from 400° C. to 150° C., above the melting point of sulphur. Therefore such a zone would allow melting of solid powdered coating material to coat the pellets. A liquid coating material comprising sulphur is most preferred as it is more easily controlled in terms of thickness and porosity of the coating.

The final product preferably comprises biochar pellets having a diameter in the range of about 0.20 mm to about 0.50 mm and a bulk density in the range of about 1.2 g/cc to about 1.5 g/cc to match commercial fertilizer.

The sulphur-containing coating can be a porous coating with minute holes over its surface. Porosity can be controlled by controlling coating thickness. It should be noted that it is possible to add chalk or other inert substances to the sulphur-containing coating to create imperfections in the coating.

It has been noted that the present biochar particles thinly coated with a sulphur-containing coating retain their granular nature, while showing improved mechanical strength, thereby reducing charcoal pulverization and preventing subsequent loss of product as dust when handled with agricultural equipment. The present coated biochar particles also reduce the hazards of dust self-ignition and potential lung contamination due to dust inhalation. In a further preferred embodiment of the present invention, bulk density of the present coated biochar particles can be adjusted by controlling coating thickness and porosity.

It should further be noted that adding inert substances, such as chalk or clay, to the sulphur blend will increase overall bulk density and create minute discontinuities in the coating resulting in greater porosity. The present method creates a biochar that mimics commercial fertilizers used in the art, and thereby allows distribution in the form of a biochar-fertilizer blend during handling and spreading.

Initially, the sulphur-containing coating covers at least a portion of the charcoal pores. However, soil bacteria rapidly break down the coating, exposing the full pore volume of the biochar, with the sulphur becoming available as a plant nutrient. The sulphur-containing coating has a temporary purpose to improve the handling characteristics of the biochar with its ultimate disposition as a plant nutrient shortly after it comes in contact with the soil. What remains for the long-term is a fully functional biochar delivered through conventional agriculture equipment.

The coating thickness and porosity can be adjusted to provide exposure of the highly porous biochar to the surrounding environment. This allows water from the surrounding soil to adsorb into the particle and aid in breakdown of the coating.

The thickness and porosity of the sulphur-containing layer can also be varied to balance biochar exposure and other desirable properties such as bulk density and mechanical strength of the coated particles.

The coated biochars of the present invention can withstand the rigours of agricultural application equipment and provide a cost-effective option of reinforcing biochar particles with firm porous coatings. The products of the present invention can be used in a variety of applications, including Matching bulk density and size of biochar particles to blend with conventional fertilizers;

Crop-specific horticulture growth media including microbial inoculates for biological crop disease control;

Specialized absorbents for soil and water decontamination; and,

Soil amendments for urban arboriculture applications and sports turf.

It should be noted that, for some uses, the incorporation of sulphur with biochar may not provide suitable mechanical characteristics. For ease of deployment and for better use of its qualities, biochar is preferably configured as small, densified, sphere shaped pellets. Preferably, these pellets have a hard outer coating so that the pellets may survive deployment by mechanical means.

In another embodiment of the invention, biochar pellets are created by mixing biochar with at least one additive and then pelletizing the resulting mixture. Experiments have shown that incorporating gluten, sulphur, lignin, or flour with biochar and following a specific procedure produces a suitable end product. Multiple procedures using different percentages of different components have been found to produce suitable biochar pellets.

In one procedure, biochar is mixed with an appropriate additive which acts as a binding or adhesion agent. The mixture is then extruded. The extrusion is then pelletized and then, optionally, shaped into spheres. The binding or adhesion agent may be one or more of the following: sulphur, lignin, or gluten. The sulphur may take the form of solid sulphur, powdered sulphur, or fine particulate sulphur. Lignin may take the form of dry material or slurry from black liquor acidulation. Gluten may take multiple forms including purified wheat gluten, fortified wheat flour or durum semolina wheat flour.

Another procedure involves, as above, mixing biochar with an appropriate additive which acts as a binding or adhesion agent. The mixture is then aggregated in a rotating pelletizer device. In one implementation, the pelletizer device is a rotating drum with an adjustable drum angle. The bottom of the drum has a rough textured surface that pulls the mixture up and around. As the mixture is tumbled repeatedly through the drum, the mixture starts to stick together in small particles which then glomerate or aggregate into larger and rounder pellets. The drum angle can be set but we use 25 degrees from horizontal. The Agglo-Miser™ device manufactured by Mars Minerals was used in one implementation. A drum angle of 25 degrees from horizontal was found to produce suitable pellets.

The following procedures have been found to produce biochar pellets with desirable characteristics:

Procedure 1:

Step 1—mix gluten with biochar and water to result in a homogenous dough-like mixture The proportions are (gluten:biochar by mass) 1:1.8. For 250 g of gluten and 450 g of biochar, 1 liter of water was used.

Step 2—pass the mixture through an extruder and cut the extrudate into pieces of between 5-10 mm in length.

Step 3—bake pieces at 70 degrees C. for approximately 60 hours.

Step 4—After cooling, the baked pieces are then placed in a spheronization device which uses heat (a maximum of 148 degrees C.) and physical force to round out the corners of the pieces. Treating the pieces in the spheronization for approximately 2 minutes provides mostly spheroid pieces with a hard outer coating.

A picture of the resulting biochar pellets is illustrated in FIG. 1.

It should be noted that for the procedures explained in this document, the amount of water used in the mixture scales up as the ingredients in the mixture similarly scale up. The use of the extruder squeezes the water from the mixture and the baking step removes the remaining water from the end product. For one implementation, a seed press was used as the extruder.

Procedure 2:

For this procedure, the steps are the same as in procedure 1 but with the following changes:

adjusting the size of the aperture on the extruder to an aperture size of between 4-6 mm;

cutting the extrudate into smaller pieces of between 3-5 mm in length; and for Step 4 is divided into 2 discrete steps:

Step 4—spin pieces in the spheronization device without heat for approximately 10 minutes Step 5—spin pieces in the spheronization device with heat for approximately 5 minutes Procedure 3:

This procedure is similar to procedure 2 with the difference that sulphur is added to the mixture. The original mixture therefore contained biochar, gluten, and sulphur with the following mass ratios (sulphur:gluten:biochar): 1:3.57:6.43. The mixture is mixed with the various components and is then processed according to the above steps. In one experiment, 450 g of biochar was mixed with 250 g of gluten, and 70 g of sulphur. The mixture was mixed with 1 liter of water. Powdered sulphur was used for this experiment but other forms of sulphur may be used. The results from procedure 3 were usable and provided acceptable pellets.

Figure 2:
Figure 3:
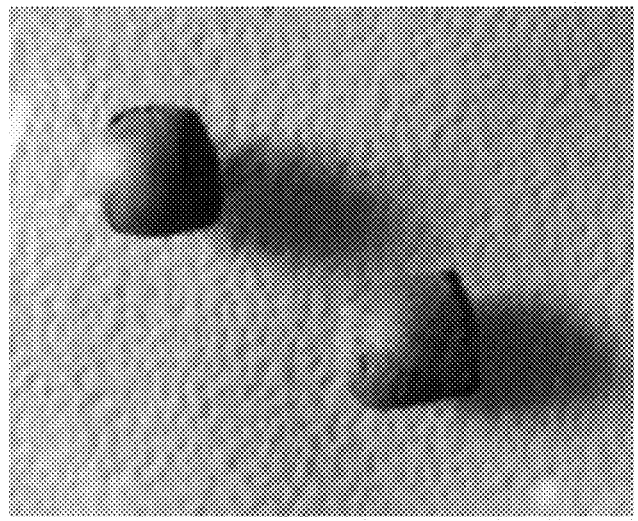

FIGS. 2 and 3 illustrated the resulting biochar pellets from procedures 2 and 3, respectively.

Figure 4:
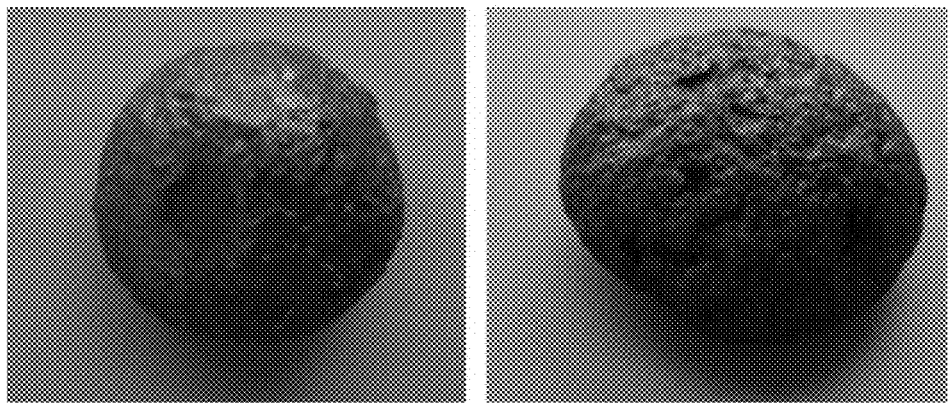

Procedure 4:

The most acceptable results were achieved using this procedure. For this procedure, biochar was mixed with sulphur and a third additive at mass percentages of 15-12.5% biochar, 75% sulphur, and 10-12.5 additive. For some experiments, the additive can be any of gluten, lignin, and flour. The pieces were baked at 140 degrees C. for approximately 60 minutes instead of the temperatures noted above. For spheronization, the spheronization device achieved a temperature of 107 degrees C. Similar to procedure 3, the pellets were spun/tumbled in the spheronization device without heat prior to being spun/tumbled with heat. An illustration of the resulting biochar pellets is presented in FIG. 4.

A further procedure involving an agglomerating mixer may also be used. For this variant, the wet mixture was added for mixing in the agglomerating mixer (e.g. an agglomerating mixer from Mars Minerals) for approximately 20 minutes. The resulting pellets were then hardened by baking.

For all of the procedures detailed above, the mixture may be pelleted using a commercial pellet mill. A commercial pellet mill should produce hard cylinders approximately the size and shape of known biochar pellets. These pellets can be re-shapeable, and may be spheronized using a hot air and random collision spheronization device. As an alternative, instead of a pellet mill, a pelletizer may be used. As noted above, a pelletizer sourced from Mars Minerals was used in one implementation.

Regarding the spheronization device, for some of the experiments, a hot air popcorn popper was used as a spheronization device. Other similar devices may, of course, be used. The spheronization device, in whichever form is used, heats the baked pieces or the pellets while forcing the pieces against each other. The pieces tumble or spin against each other and, in doing so, rounds out the pellets. Spheronizers, also known as marumizers, sourced from Caleva Process Solutions Ltd. (www.caleva.com) may also be used.

It should be noted that the biochar used in the experiments may be produced in any number of ways. The process disclosed above for producing sulphur coated biochar may be used as well as the process disclosed Dekhoda, A. M. in Developing Biochar-Based Catalyst for Biodiesel Production. For greater clarity, this process may involve the steps of initially drying the biochar for 18 hours at 140 C before derivatization. As an example of a sulfonation: 10.2 g of biochar (1-2 mm sieve size) is placed into a 125 mL round bottom flask fitted with a reflux condenser. Then, 25 g of fuming sulfuric acid is added with stirring. The slurry is heated to 60 C for 2 hours, then to 150 C for 1 hour. The product is worked up by repeated washing with cold water, followed by drying overnight in an oven at 80 C. For more technical information regarding the process for producing biochar and its uses, the following documents (all of which are incorporated herein by reference) may be consulted:

a) Yu J T, Dehkhoda A M, Ellis N. (2011) Development of Biochar-based catalyst for Transesterification of Canola Oil. Energy Fuels 25, 337-344;

b) http://cfpub.epa.gov/ncer_abstracts/index.cfm/fuseaction/ display.abstractDetail/abstract/9125/report/F;

c) Kastner J R, Miller J, Geller D P, Locklin J, Keith L H, Johnson T. (2012) Catalytic esterification of fatty acids using solid acid catalysts generated from biochar and activated carbon. Catalysis Today 190, 122-132;

d) Dehkhoda A M, West A H, Ellis N. (2010) Biochar based solid acid catalyst for biodiesel production. Applied Catalysis A: General 382, 197-204;

e) Kastner J R, Geller D, Keith L H. (2010) Solid acid catalysts, methods of making, and methods of use. United States Patent Application Publication US2010/0312008 A1 9 Dec. 2010

In one example, the biochar is sulfonated and then converted to pellets by the above procedures involving biochar/ gluten and extrusion/spheronization. In another example, biochar pellets are made using the biochar/gluten, extrusion/ spheronization method and, afterwards, the biochar pellets are sulfonated in the manner described above. In both cases, the sulfonated biochar is used as a solid, heterogeneous acid catalyst. While one application of these sulfonated biochar pellets is the esterification of free fatty acids in waste cooking oil, one can see how acid-catalysed esterification reactions can be generally considered.

As noted above, the resulting biochar pellets may be used in the manufacture of biodiesel. These biochar pellets may also be used in esterifications and transesterification reactions other than biodiesel manufacture. The biochar pellets may also be used as a convenient biodiesel desiccant. Alternatively, un-densified biochar may also be used in a sealed cartridge or similar as a disposable fixed bed biodiesel desiccant. Accordingly, it should be clear that the resulting product may be used as a biodiesel desiccant, a transportation fuel desiccant, a dessicant for liquid hydrocarbon mixture, or as an organic solution desiccant.

The advantages of the resulting biochar pellets are numerous. These biochar pellets manufactured using the above procedures are inert to biodiesel at room temperature, i.e. they do not catalyze or react chemically with biodiesel. As another advantage, these biochar pellets absorb unwanted biodiesel contaminants such as water and glycerol. The biochar pellets also maintain their shape and do not dissolve (up to 48 hours tested), so the pellets are easily removed from the biodiesel. The shape and size of the pellets lends itself to convenient large-scale processing options, such as fixed-bed flow through reactors in which the biochar desiccant remains stationary and the biodiesel is passed through the resin bed. The biochar desiccant, when spent, can be disposed of harmlessly in landfills as a bio-based product.

The biochar pellets and the sulfonated biochar product may also be used for other purposes. As an example, the end product may be used as a supplement for animal feed. Activated charcoal is known to be effective at treating parasitic infections in different ruminant animals, including cattle and sheep (see) Naka, K., et al. "Adsorption Effect of Activated Charcoal on Enterohemorrhagic *Escherichia coli*," J. Vet. Med. Sci 63(3): 281-285, 2001, and see Watarai, S., et al. "Feeding Activated Charcoal from Bark Containing Wood Vinegar Liquid (Nekka-Rich) is Effective as Treatment for Cryptosporidiosis in Calves," J. Dairy Sci. 91:1458-1463, 2008. Therapeutic variants are sold commercially where charcoal is combined with various sulphaletamides for the treatment of coccidiosis infection in beef cattle, dairy cattle, veal and sheep. Research has shown that adding charcoal to the diet of chicken broilers and laying hens can improve growth performance during the first 28 days of fattening and reduced cracked eggs if added as a dietary supplement to laying hens (see Kutlu, H-R., Unsal, I., Gorgulu, M., Animal Feed Science and Technology, 2001, vol 90, n3-4, pp. 213-226. ISSN 0377-8401.).

It is also widely known that adding sulphur as a dietary supplement can improve ruminant health if the animals are raised in areas where the soils have low quantities of the mineral. Sulphur is an essential element for ruminal microorganism production of vital amino acids, vitamins and enzymes, (see Morrison, M., Murray, R. M., and Boniface, A. N., 1990. Nutrient metabolism and rumen micro-organisms in sheep fed a poor quality tropical grass hay supplemented with sulphate. J. Agri. Sci. Camb. 115:269-275.). The sulphur can be used in a compound state (e.g. sodium sulfate), or in its elemental form with near equal effectiveness, (see Tisdale, S. L., 1977. Sulphur in forage quality and ruminant nutrition, Technical Bulletin no. 22. The Sulphur Institute.). Adding sulfur has been found to improve milk production, increase beef cattle weight gain (see Hill, G. M., et al., 1984. Effect of Sulphur levels in Urea-treated corn silage diets. Sulphur in Agriculture. 8: 8-10.), and wool and meat production in sheep.

A person understanding this invention may now conceive of alternative structures and embodiments or variations of the above all of which are intended to fall within the scope of the invention as defined in the claims that follow.

We claim:

1. A method for producing biochar pellets, the method comprising:
    a) mixing biochar with at least one additive and water to result in a mixture;
    b) extruding said mixture to result in an extrudate;
    c) cutting said extrudate into pellets;
    d) heating said pellets for 60 hours at 70 degrees C. and then cooling said pellets; and
    e) processing said pellets in a spheronization device which heats said pellets and forces said pellets to tumble against one another while being heated.

2. A method according to claim 1 wherein said at least one additive is selected from the group consisting of: gluten, sulphur, and lignin.

3. A method according to claim 1 wherein said biochar is produced according to a method comprising:
    feeding a biomass feedstock to a pyrolysis reactor, to pyrolize the feedstock into biochar particles;
    size-sorting the biochar particles; and
    coating the biochar particles with a coating material comprising sulphur.

4. A method according to claim 2 wherein said mixture has a composition selected from the group consisting of:
    a gluten: biochar by mass ratio of 1:1.8; and
    a sulphur:gluten:biochar by mass ratio of 1:3.57:6.43.

5. A method according to claim 2 wherein said mixture has a composition of 15-12.5% biochar, 75% sulphur, and 10-12.5% additional additive, said composition being determined by mass percentage of a total mass of said mixture.

6. A method according to claim 5 wherein said additional additive is selected from the group consisting of: lignin, gluten, and flour.

7. A method according to claim 1 wherein step e) comprises the steps of:
    spinning said pellets in said spheronization device without heat for approximately 10 minutes; and
    spinning said pellets in said spheronization device with heat for approximately 5 minutes.

8. A method according to claim 1 wherein said spheronization device heats said pellets to a temperature between 70 degrees C. and 148 degrees C.

9. A method for producing biochar particles containing at least one additive, said method comprising the steps of:
    a) feeding a biomass feedstock to a pyrolysis reactor, to pyrolize the feedstock into biochar particles;
    b) size-sorting the biochar particles;
    c) mixing said biochar particles with said at least one additive and water to result in a mixture;
    d) extruding said mixture to result in an extrudate;
    e) cutting said extrudate into pellets;
    f) heating said pellets for 60 hours at 70 degrees C. and then cooling said pellets;
    g) processing said pellets in a spheronization device which heats said pellets and forces said pellets to tumble against one another while being heated;
    wherein said at least one additive is selected from the group consisting of: gluten, sulphur, and lignin.

10. The method of claim 9, wherein said at least one additive is in a form selected from the group consisting of a liquid and a powdered solid.

11. The method of claim 9, wherein said at least one additive is for modifying bulk density and porosity of said pellets.

* * * * *